United States Patent [19]

Muramatsu et al.

[11] 4,260,680

[45] Apr. 7, 1981

[54] METHOD AND APPARATUS FOR THE MEASUREMENT OF GLUCOSE CONTENT

[75] Inventors: Kozo Muramatsu, Machida; Kuniko Samizo, Tachikawa, both of Japan

[73] Assignee: Mitsubishi Chemical Industries, Ltd., Tokyo, Japan

[21] Appl. No.: 949,130

[22] Filed: Oct. 6, 1978

[30] Foreign Application Priority Data

Oct. 22, 1977 [JP] Japan .................................. 52/127102

[51] Int. Cl.³ .......................... C12Q 1/54; C12Q 1/26; C12M 1/34

[52] U.S. Cl. .......................................... 435/14; 435/25; 435/180; 435/181; 435/291; 204/1 T; 204/195 B

[58] Field of Search ................. 435/14, 174, 288, 291; 195/103.5 R, 103.5 C, 127; 204/195 B, 1 T

[56] References Cited

U.S. PATENT DOCUMENTS

| | | | |
|---|---|---|---|
| 3,421,982 | 1/1969 | Schultz et al. ...................... | 435/14 X |
| 3,902,970 | 9/1975 | Levin .................................. | 435/14 X |
| 3,937,615 | 2/1976 | Clack et al. ......................... | 435/14 X |
| 4,033,830 | 7/1977 | Fletcher .............................. | 204/1 T |
| 4,059,406 | 11/1977 | Fleet .................................. | 204/1 T X |
| 4,085,009 | 4/1978 | Pace ................................... | 204/195 B |

OTHER PUBLICATIONS

Ramaswamy et al., *Chemical Abstracts*, 80:105563r, (1974).
Bloxam, *Chemical Abstracts*, 81:60227m, (1974).
Ramaswamy et al, *Indian J. Biochem. Biophys.*, 10(2), 96-98, (1973).
Bloxam, *Biochem. Med.*, 10(1), 61-69 (1974).

*Primary Examiner*—Alvin E. Tanenholtz
*Attorney, Agent, or Firm*—Oblon, Fisher, Spivak, McClelland & Maier

[57] ABSTRACT

A method and apparatus for measuring the glucose content in a liquid sample by passing the sample consecutively through a column of at least one ion exchange resin and a column of immobilized glucose oxidase and then determining the amount of hydrogen peroxide produced by contacting the sample with glucose oxidase.

11 Claims, 7 Drawing Figures

METHOD AND APPARATUS FOR THE MEASUREMENT OF GLUCOSE CONTENT

BACKGROUND OF THE INVENTION

1. Field of the Invention

This invention relates to a method and apparatus for the measurement of glucose content. More particularly, this invention relates to a method for the measurement of the sugar content in a liquid sample such as serum or urine by determining the amount of hydrogen peroxide produced by contacting the sample with glucose oxidase.

2. Description of the Prior Art

There is a continuing need for rapid, accurate and quantitative determinations of the glucose content in body fluids. In clinical diagnosis, it is important to analyze the glucose content of serum (blood glucose) or that of urine (urine glucose).

Accordingly, various methods have been proposed for analyzing blood or urine glucose simply and rapidly. Among these, one of the most preferred methods is one in which the glucose content of a liquid sample such as serum is analyzed by contacting the liquid sample with glucose oxidase to produce hydrogen peroxide and determining the amount of hydrogen peroxide produced through detection electrodes to which a certain DC voltage is applied, since according to this method highly precise results can be obtained with easy operation.

However, the above-mentioned glucose analysis method is disadvantageous in that in the course of repeated analyzing procedures some proteins or non-glucose reducing substances present in a liquid sample such as serum or urine come to inhibit the enzyme activity or contaminate the detection electrodes and thereby decrease its detection sensitivity so that accuracy of the analysis gradually decreases.

SUMMARY OF THE INVENTION

It has now been discovered that when the liquid sample is pretreated with an ion exchange resin, it can be effectively freed of any substance either inhibiting the enzyme activity or adversely affecting the sensitivity of the detection electrodes. It also has now been found that the decrease in detection sensitivity can be fully prevented by contacting the ion exchange resin-treated liquid sample with glucose oxidase and determining the hydrogen peroxide produced by the use of detection electrodes to which an alternating voltage of rectangular wave form is applied.

Accordingly, it is an object of this invention to provide a method for repeatedly analyzing the glucose content of liquid samples such as serum or urine with high precision and reproducibility. This object can be accomplished by a glucose analysis method in which the glucose content of a glucose-containing liquid sample is analyzed by contacting the liquid sample with glucose oxidase to produce hydrogen peroxide and determining the amount of hydrogen peroxide produced, said method being characterized by (1) pretreating the liquid sample with an ion exchange resin prior to contacting with glucose oxidase and (2) following contacting the pretreated liquid sample with glucose oxidase, determining the amount of hydrogen peroxide thus produced by the use of detection electrodes to which a voltage of rectangular wave form is applied.

BRIEF DESCRIPTION OF THE DRAWING

FIGS. 1(1), 1(2) and 1(3) show wave forms of a typical rectangular alternating voltage, measured current and measuring signal, respectively, useful in the method of this invention;

FIGS. 2(1), 2(2), and 2(3) show another set of wave forms similar to FIG. 1(1), 1(2) and 1(3);

FIGS. 7(1), 7(2), 7(3) and 7(4) illustrate a change with the passage of time during the operation of Example 2 in a voltage applied to a working electrode, a current flowing through the working electrode, and states of discharge-suction of pumps for water and a buffer solution, respectively, in which + denotes discharge and − denotes suction.

DETAILED DESCRIPTION OF THE PREFERRED EMBODIMENTS

In the method of this invention, it is essential that a liquid sample be pretreated with an ion exchange resin. As the liquid sample, usually, a body fluid containing glucose in a small amount on the order of 20 to 1,000 mg/dl, such as serum, urine or the like is used.

When the glucose concentration of the sample is relatively high, it is preferred to dilute the sample to an appropriate concentration, for example, in the range of 5 to 300 mg/dl of glucose, from the viewpoint of enzyme activity and detection sensitivity.

Body fluids such as serum and urine contain some proteins and non-glucose reducing substances. For example, serum and urine contain such proteins as albumin and globulin, and the amount of albumin present in the serum of a normal person is about 3.5 g/dl. These proteins suppress the activity of glucose oxidase and reduce its life time.

Serum and urine also contain such non-glucose reducing substances as uric acid, glucuronic acid, ascorbic acid and glutathione, which generate some oxidation currents at a given applied voltage, thereby adversely affecting the determination of hydrogen peroxide through detection electrodes. Thus, these substances are responsible for positive errors in the resulting data.

The harmful proteins and non-glucose reducing substances can be effectively removed by adsorbing them on an ion exchange resin. Preferably, the ion exchange resin used is a strongly basic anion exchange resin alone or in combination with a strongly acidic cation exchange resin. Thus, part of the proteins and substantially all the non-glucose reducing substances in the body fluid are adsorbed on the strongly basic anion exchange resin and removed from the body fluid, and the strongly acidic cation exchange resin may be used to adsorb thereon and remove the remaining proteins and other contaminants which cannot be adsorbed on the strongly basic anion exchange resin.

As the strongly acidic cation exchange resin, various known resins such as those having a matrix of styrene-divinylbenzene copolymer to which sulfonic acid groups are introduced as ion exchange groups may be used. Exemplary of such cation exchange resins are Diaion SK1B; Diaion SK 102, 103, 104, 106, 110, 112 and 106; Diaion PK 208, 212, 216, 220, 224 and 228 (Diaion is a registered trademark of Mitsubishi Chemical Industries, Ltd.); Amberite 200, Amberite IR 120 (Amberite is a registered trademark of Rohm and Haas) and the like.

While the ion exchange groups of these resins may be in the form of free acid (H-form), preferably they are used in the salt form (e.g., Na-form).

As the strongly basic anion exchange resins, various known resins such as those having a matrix of styrene-divinyl-benzene copolymer to which quarternary ammonium groups are introduced as ion exchange groups may be used. Specific examples of such resins are Diaion PA 304, 310, 318, 404, 410 and 418; Diaion SA 10A and 11A; Diaion HPA 10, Amberite IRA 458 and the like.

Also, while the ion exchange groups of these resins may be in the form of free base (OH-form), they are preferably used in the salt form (e.g., chloride-form).

Of the above-described ion exchange resins, those having large capacity such as porous, highly porous and macroreticular ion exchange resins are more preferred than gel-type ion exchange resins.

Suitable particle diameters of these cation and anion exchange resins are in the range of 20 to 100 mesh (JIS mesh size). As the particle diameter decreases, the absorption efficiency increases but a pressure drop in the resin column increases. Therefore, the preferred particle diameters are in the range of 20 to 60 mesh.

Treatment of a liquid sample with a strongly acidic cation exchange resin and a strongly basic anion exchange resin can be performed by passing the sample through a column or columns packed with these resins. For this purpose, it is preferred that a plurality of columns of single bed system be used which are packed separately with the strongly acidic cation exchange resin and the strongly basic anion exchange resin and which are connected in series with each other.

In a preferred embodiment of this invention, a liquid sample is passed first through a strongly basic anion exchange resin and then through a strongly acidic cation exchange resin.

Alternatively, a column of mixed bed system packed with a mixture of the two types of ion exchange resins may be used. In a preferred embodiment, the first half of the column is packed with a strongly basic anion exchange resin, and the latter half of the column is packed with a strongly acidic cation exchange resin.

Each of the anion and cation exchange resins is used in an amount (by volume) about 20 to 300 times the volume of the liquid sample passed through the column at a time. If the glucose concentration of the liquid sample is in the range of 5 to 300 mg/dl, 5 to 500 $\mu$l of the sample is preferably passed at a time.

In general, the volume of the anion exchange resin to be used is substantially the same as that of the cation exchange resin.

When the ion exchange resin loses its capability for removing proteins and non-glucose reducing substances after repeated passage of liquid samples therethrough, usually it is renewed or replaced by a new one.

The amount of the liquid sample which can be treated until the resin loses its capability depends upon the resin and the liquid sample to be used. When the sample is serum, the use of a suitable resin makes possible the treatment of normally 150 to 300 times as much the sample as each resin by volume, and in some cases, a larger amount of the sample can be treated.

A used resin on which proteins and non-glucose reducing substances have been adsorbed may be treated with an acid or alkali so as to regenerate it and make it suitable for reuse.

Following the treatment with an ion exchange resin, the liquid sample is brought into contact with glucose oxidase, whereby the glucose in the sample is oxidized to gluconic acid while producing hydrogen peroxide.

If sufficient oxygen is present in the reaction system and the pH of the system is kept within a fixed range, the amount of hydrogen peroxide produced is proportional to the amount of glucose in the liquid sample.

If a sufficient amount of oxygen is not present in the reaction system, air may be supplied to the liquid sample through the use of a pump or the like either in a continuous or discontinuous manner.

Alternatively, in place of supplying air a sufficient amount of oxygen may in advance be dissolved in the liquid sample or the liquid which is introduced into the system.

In order to maintain the pH within a given range, a buffer solution (e.g. phosphate or acetate buffer) may be added to the sample liquid, if necessary.

Usually, the buffer solution, the concentration of which ranges from about 0.1 M to about 1 M is used in an amount enough to dilute the liquid sample approximately 2 to 10 times.

As the glucose oxidase enzyme, those produced from the cells of the microorganisms such as the genus Aspergillus and the like may be used. Particularly, in the case of using the enzyme which has been extracted from the cells of the microorganism, it is advantageous to immobilize the enzyme in a conventional manner prior to its use.

The immobilization of glucose oxidase can be effected by conventional means such as ionic bonding, covalent bonding or entrapping method.

According to the ionic bonding method, an aqueous glucose oxidase solution to which a buffer solution (e.g., 0.1–1 M phosphate buffer) is added may be contacted with an ion exchanger including an anion exchange resin such as Diaion PA 310, a porous-type anion exchange resin, to adsorb and immobilize the glucose oxidase on the resin.

In a typical procedure of the entrapping method, a hydrophilic polymer such as polyvinyl alcohol, polyvinylpyrrolidone or the like, an organic compound having at least two photopolymerizable functional groups such as methylene-bisacrylamide or the like, and glucose oxidase are dispersed uniformly in a solvent such as water. Following evaporation of the solvent, a film of the mixture is deposited on an appropriate support such as glass beads of about 20 to 100 mesh, which is then irradiated with light to cross-link the polymer and immobilize the glucose oxidase.

According to the covalent bonding method, glass beads having silanol groups are treated consecutively with $\gamma$-amino-propyltriethoxysilane and glutaraldehyde to combine the propylamino group with one of the two formyl groups of the glutaraldehyde. The immobilization of glucose oxidase can be accomplished by combining an amino group of glucose oxidase with the other formyl group of the glutaraldehyde.

For the immobilization of glucose oxidase according to these methods, the preferred particle diameters of supports are in the range of 20 to 100 mesh.

The liquid sample can be contacted with glucose oxidase, for example, by passing the sample through a column packed with the glucose oxidase immobilized as above. The contact time of the sample with glucose oxidase is preferably from 1 to 30 seconds, and more preferably from 1 to 10 seconds. As the activity of the immobilized enzyme per unit volume increases, the contact time decreases.

The glucose oxidase is used in an amount sufficient to oxidize at least 5 to 10% of the total glucose present in the liquid sample to gluconic acid and hydrogen peroxide.

The amount of hydrogen peroxide produced by contacting the liquid sample with glucose oxidase is measured through detection electrodes to which an appropriate voltage is applied. Since hydrogen peroxide generates an oxidation current having an intensity directly proportional to the amount thereof at an applied voltage in a specific range, the amount of hydrogen peroxide can be determined by measuring the oxidation current through detection electrodes connected with an ammeter.

As previously mentioned, the amount of hydrogen peroxide is directly proportional to the amount of glucose in the liquid sample, as well. Hence, it is possible to analyze the amount of glucose from the amount of hydrogen peroxide determined as above.

As the detection electrodes, either of the two and three electrode systems can be used.

In both the systems, the working electrode and the counter electrode are usually made of platinum, gold, carbon or the like. The reference electrode is a Ag-AgCl or calomel electrode.

In the prior art method, a direct current voltage on the order of 0.4 to 0.7 is usually applied to the detection electrodes.

In the method of this invention, it is favorable to apply an alternating voltage of rectangular wave form instead of the DC voltage.

As previously mentioned, most of the proteins and non-glucose reducing substances are adsorbed on and removed from one or more ion exchange resins, but in some cases part of the proteins and other contaminants remain in the liquid sample without being adsorbed on the resins.

If under such situation a voltage is applied to the detection electrodes, the residual proteins and other contaminants are deposited on the measuring electrode, decreasing the detection sensitivity of the electrode.

The proteins and other contaminants deposited on the measuring electrode can be removed from the electrode by reversal of polarity. After the contaminants have been removed from the measuring electrode, the polarity is again reversed. Thus, the use of such a voltage as to change its polarity alternately, namely, an alternating voltage makes it possible to remove any protein or contaminants deposited on the measuring electrode or in other words to prevent the residual protein or contaminants from depositing on the measuring electrode.

When an alternating voltage is applied to the detection electrodes, they function like a condenser. As a result, immediately after the change in polarity of voltage a condenser current attributable to the applied alternating voltage is generated and flows through the circuit including the detection electrodes, ammeter and voltage applying unit. Consequently, the sum of the oxidation current attributable to the generation of hydrogen peroxide and the condenser current is read on the ammeter. However, the condenser current rapidly declines with time and ultimately disappears so that the net oxidation current can be determined by reading the current after disappearance of the condenser current.

By way of example, when an alternating voltage of rectangular wave form as shown in FIG. 1(1) having positive voltage $V_1$ (volt), positive voltage application time $t_1$ (second), negative voltage $V_2$ (volt), negative voltage application time $t_2$ (second) and period T (second) is applied to a measuring electrode, a current having a form as shown in FIG. 1(2) is obtained in response to the applied alternating voltage. Then, the time, $\theta'$ (second) taken from the generation of a condenser current to the disappearance thereof is considered and the current response between time $\theta$ (sec.) ($\theta > \theta'$) after each change of polarity into positive and the time just before the next change into negative is isolated as a measuring signal, from which the net oxidation current can be read directly.

In order to remove any protein or other contaminant deposited on the measuring electrode or even prevent the deposition of such contaminants, a negative voltage selected appropriately in the range of $-0.1$ to $-1.2$ volt, preferably $-0.5$ to $-0.3$ volt may be applied to the electrode.

When the liquid sample flows continuously, it is possible to perform either the cleaning of the electrode or the measurement of oxidation current at each polarity by using as the working electrode and the counter electrode the same type of measuring electrodes which are made of the same material and which have the same form and applying to the electrodes an alternating voltage of rectangular wave form in which the hights of the positive and negative voltages are equal to each other.

By way of example, a typical voltage wave form applied in such cases and the resulting current measured and measuring signal isolated by the above-mentioned procedure are shown in FIG. 2(1), (2) and (3), respectively. In FIG. 2, $V_1$ and and $V_2$ represent a positive and negative voltage, respectively, and T represents a period in second. In order to derive a current and measuring signal in the form as shown in FIG. 2, one may use, for example, the apparatus shown in FIG. 3.

Figure 1:
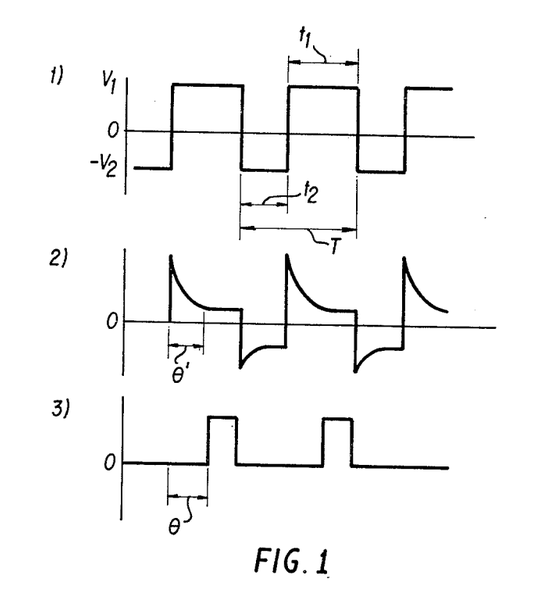
Figure 2:
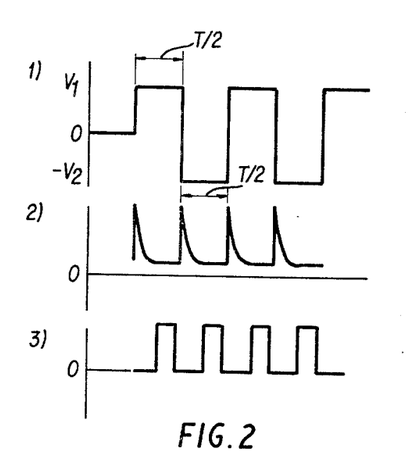
Figure 3:
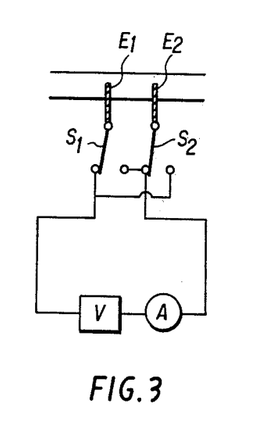
FIG. 3 shows an embodiment of the apparatus which is used in the method of this invention for applying a voltage to detection electrodes.

Referring to FIG. 3, the apparatus involves a DC voltage applying unit V, an ammeter A, changeover swiches $S_1$ and $S_2$ and a pair of detection electrodes $E_1$ and $E_2$ which serve as a measuring electrode and a counter electrode alternately. Each of switches $S_1$ and $S_2$ is transferred in the direction of the arrows alternately at regular intervals preset by a timer (not shown). Thus, by the use of this apparatus, it becomes feasible to apply a voltage of rectangular wave form as shown in FIG. 2(1), with which a current is detected in the wave form as shown in FIG. 2(2) and a measuring signal as shown in FIG. 2(3) is in turn derived from the current.

If the frequency of the applied alternating voltage is excessively high, a high condenser current occurs throughout the entire period of one Hertz and it is impossible to detect the oxidation current separate from the condenser current during one Hertz because, in addition to the oxidation current, the condenser current is detected. When such excessively high frequency of the alternating voltage is applied, the difference between the currents detected under the same conditions for a sample containing glucose and for a sample having a similar composition and not containing glucose can be taken as the oxidation current.

When the frequency of the applied alternating voltage is higher than 10 Hertz such a method of detecting the oxidation current is adopted.

On the other hand, when the frequency of the applied alternating voltage is low, it is unnecessary to adopt such a detection method, because the oxidation current can be detected separate from the condenser current during one Hertz with high precision.

In general, the frequency is selected from the range of 0.001 to 50 Hz, preferably 0.004 to 5 Hertz.

Thus, the above-mentioned procedure permits detection of the oxidation current in response to the amount of glucose in a liquid sample. The actual determination of glucose in a particular liquid sample can be performed with a calibration curve which is prepared by measuring oxidation currents with different glucose solutions of known concentrations or with a standard sample having a composition similar to that of the liquid sample to be measured such as a standard serum and deriving a relationship between the amount of glucose in a liquid sample and the oxidation current detected.

As hereinbefore described in detail, in accordance with this invention, liquid samples such as serum, urine or the like can be freed of proteins and non-glucose reducing substances and detection electrodes can be effectively protected from deposition of any protein or contaminants thereon so that the glucose analysis system can be used repeatedly while keeping its high accuracy and reproducibility.

Having generally described the invention, a more complete understanding can be obtained by reference to certain specific examples, which are included for purposes of illustration only and are not intended to be limiting unless otherwise specified.

EXAMPLE 1

Figure 4:
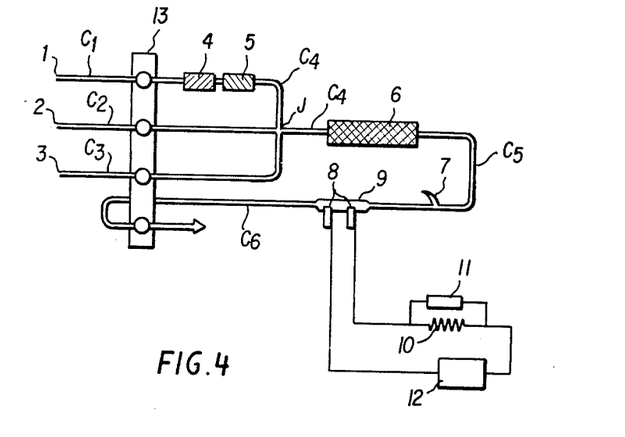
FIGS. 4 to 6 are schematic diagrams by glucose analysis apparatus, which involve sample inlet 1, buffer inlet 2, air inlet 3, anion exchange resin column 4, cation exchange resin column 5 and glucose oxidase column 6.

The glucose content of serum is analyzed with the apparatus shown in FIG. 4.

Referring to FIG. 4, there is shown an apparatus which involves sample inlet 1, buffer inlet 2 and air inlet 3, through which the two liquids and air are pumped to their respective conduits $c_1$, $c_2$ $c_3$ by means of common pump 13. The apparatus also involves anion exchange resin column 4, cation exchange resin column 5, glucose oxidase column 6, air vent 7, detection electrodes 8, measuring cell amperometric detector) 9, resistor 10, recording ammeter 11 and voltage applying unit 12. Conduit $c_4$ joins the glucose oxidase column 6 to the cation exchange resin column 5. Buffer conduit $c_2$ and air conduit $c_3$ join conduit $c_4$ at location J. Conduit $c_5$ joins column 6 to the amperometric detector 9 and conduit $c_6$ is the exit column for the sample flowing through the detector.

Each ion exchange column is 4 mm in inner diameter and 12 cm in length. Column 4 is packed with Diaion PA 310 (Cl-form), a porous anion exahange resin which has been washed with deionized water, while column 5 is packed with Amberite 200 (Na-form), a cation exchange resin which has been subjected successively to washing with deionized water, transformation into the H-form with 2 N hydrochloric acid, returning to the Na-form with aqueous 2 M sodium chloride and final washing with deionized water.

As the glucose oxidase column, a glass column of 4 mm in diameter and 15 cm in length is used and packed with glucose oxidase which has been immobilized according to the procedure described hereinafter. The conversion of glucose in the glucose oxidase column is about 8% as determined by the procedure also described hereinafter.

As the detection electrodes, two platinum electrodes of 1 mm diameter are used to function as either the measuring or counter electrode, and placed in the amperometric detector so as to provide an electrode gap of 10 mm. An alternating voltage of rectangular wave form having a positive and negative voltage of 0.6 volt and a frequency of 0.006 Hz is applied to the detection electrodes.

The current flowing through the circuit involving the detection electrodes is detected by the ammeter as a voltage drop caused by the resistor connected to the circuit in series and recorded on the recorder of the ammeter.

The liquid samples used are two serum samples, Stable A, lot No. 403358 and Stable N, lot No. 403360 (Stable is a registered trademark of Chugai Pharmaceutics Co., Ltd.), both diluted about ten times by weight with deionized water prior to analysis.

Using an autosampler (not shown), 280 $\mu$l portions of the two diluted serum samples are alternately introduced at intervals of about 3 minutes through the sample inlet into the sample tube (with sample supplying periods of 14 seconds, and at all times except this sample supplying periods water is introduced into the sample tube). Air and a 0.5 M phosphate buffer solution (pH 6.0) are supplied through the air inlet and the buffer inlet, respectively.

The feed rates of the liquid sample, buffer solution and air are regulated by the pump to 1.2 ml/min., 0.8 ml/min. and 0.6 ml/min., respectively.

The feeding of liquid samples is repeated ninety times in this manner and the glucose content of each sample is analyzed. Three aqueous glucose solutions having concentrations indicated in Table 1 below are then fed as liquid samples one after another through the sample inlet and the oxidation currents generated are measured through the detection electrodes. The data thus obtained are given in Table 1. Table 1 also includes the data of oxidation current obtained in a test which is conducted with the same glucose solutions prior to the repeated feeding of the serum samples.

TABLE 1

| Concentration of glucose solution | Oxidation current | |
|---|---|---|
| | Before feeding of serum samples | After feeding of serum samples |
| A: 10 mg/dl | 0.070 | 0.070 |
| B: 20 mg/dl | 0.135 | 0.140 |
| C: 30 mg/dl | 0.208 | 0.200 |

As is apparent from Table 1, after the feeding of liquid sample and the glucose analysis thereof have been repeated ninety times, no decrease in activity of glucose oxidase and in electrode sensitivity is recognized so that the oxidation current responding to the amount of glucose can be detected with high accuracy and reproducibility.

Subsequently, the above-mentioned two serum samples are fed to the apparatus and the oxidation currents are determined in the same manner as described above.

On the other hand, a calibration curve which indicates the relationship between the glucose content of a glucose solution and the oxidation current detected with the solution is prepared in order to determine the amount of glucose in a given liquid sample. On the basis of this calibration curve, the amounts of glucose in the foregoing two serum samples are evaluated. The results are shown in Table 2 below.

For comparison, in Table 2 is included the data obtained by analyzing the glucose concentration of the serum samples according to the enzymatic colorimetric method described hereinafter in detail.

TABLE 2

| Serum sample | Glucose concentration of sample (mg/dl) | |
|---|---|---|
| | Method of this invention | Enzymatic colorimetry |
| Stable A | 22.8 | 22.8 |
| Stable N | 14.5 | 14.3 |

It is apparent from Table 2 that the data derived by the method of this invention are in close agreement with those obtained by the enzymatic colorimetry.

(1) Preparation of immobilized glucose oxidase

A photosensitive polymer solution is prepared by mixing 12.5 g of aqueous 10 weight percent polyvinylpyrrolidone, 1 g of pentaerythritol triacrylate, 0.139 g of benzoin methyl ether, 0.069 g of sodium dodecylsulfate and 2.5 g of methyl cellosolve.

A 0.5 g aliquot of the photosensitive solution is mixed with 0.5 ml of a 0.1 M phosphate buffer solution (pH 6.0) containing 10 mg of glucose oxidase and the mixture is stirred for 10 minutes.

Glass beads (3 g) of 0.8 mm diameter are then added to the mixture and thoroughly mixed therewith. The resulting liquid-beads mixture is then poured onto a screen of 80 to 100 mesh, through which a portion of the liquid is allowed to fall. The glass beads having the liquid deposited thereon are spread uniformly on the screen and placed in a desiccator at room temperature to evaporate the solvent. After evaporation of the solvent, the glass beads are exposed in air to the light of a 2 KW superhigh pressure mercury lamp (wavelengths ranging from 300 to 500 nm; bright line spectra at 365 nm, 405 nm and 436 nm) from a distance of about 50 cm for 5 minutes to immobilize the glucose oxidase.

The thus obtained glass beads having immobilized glucose oxidase deposited thereon are then filled in a glass column of 4 mm in inner diameter and 15 cm in length to provide a glucose oxidase column.

(2) Determination of the conversion of glucose in a glucose oxidase column

Figure 5:
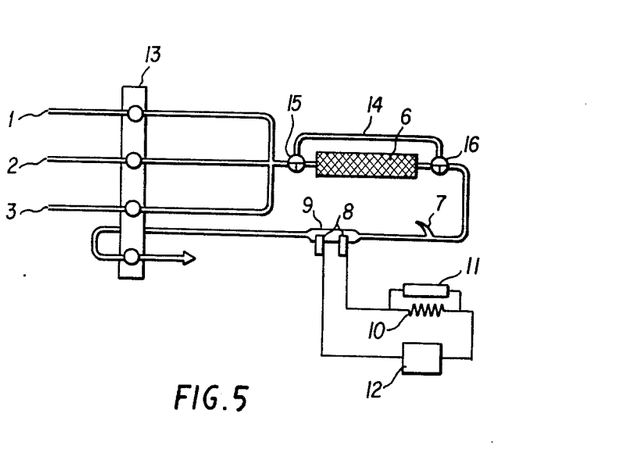

The apparatus used is the same as shown in FIG. 4 except that the ion exchange resin columns are omitted and a bypass tube is attached so as to bypass the glucose oxidase column (said apparatus being shown in FIG. 5 wherein the FIGS. 1 through 13 denote the same members as in FIG. 4 and the FIG. 14 denotes the bypass tube and FIGS. 15 and 16 denote bypass cocks).

At first, 280 μl of an aqueous 1.1 mM hydrogen peroxide solution (which is equivalent to the amount of hydrogen peroxide produced by he entire oxidation of glucose present in 280 μl of a liquid sample containing 20 mg/dl of glucose) is fed as a liquid sample through the sample inlet with bypass cocks 15 and 16 being open, and under a DC voltage of 0.6 volt the oxidation current ($I_1$) is determined through the detection electrodes. Bypass cocks 15 and 16 are then closed and 280 μl of an aqueous glucose solution containing 20 mg/ml of glucose is fed through the sample inlet and allowed to pass through the glucose oxidase column. Also under a DC voltage of 0.6 volt, the oxidation current ($I_2$) generated with the glucose solution is determined through the detection electrodes.

The conversion of glucose in the glucose oxidase column is calculated by the following equation:

Conversion (%) = ($I_2/I_1$) × 100

(3) Enzymatic colorimetry

The above-mentioned serum samples, Stable A and Stable N are diluted about ten times by weight with deionized water. To 1 ml aliquot of each dilute sample, 4 ml of an aqueous 1 weight percent solution of "GOD-PODLK", a trademark of Nagase Sangyo for a glucose determination reagent which contains glucose oxidase, 4-aminoantityrine and peroxidase, and 4 ml of an aqueous 0.1 weight percent phenol solution are added and stirred. The mixture is then allowed to stand for 15 minutes at 40° C. so as to effect the oxidative condensation reaction between phenol and 4-aminoantipyrine, whereupon it is cooled on a water bath and allowed to stand for 15 minutes. Thereafter, the amount of glucose in the sample is analyzed colorimetrically by comparison of absorbance at 505 nm.

COMPARATIVE EXAMPLE 1

Using the apparatus shown in FIG. 5, a DC voltage of 0.6 volt is applied to the detection electrodes with bypass cocks 15 and 16 being closed.

To the apparatus 280 μl of an aqueous glucose solution containing 20 mg/dl of glucose is fed through the sample inlet and the oxidation current generated is determined.

Then 280 μl portions of two liquid samples prepared by diluting the serum samples, Stable A and Stable N, in the same manner as described in Example 1 are fed alternately through the sample inlet. At each time when the feeding of serum sample has been repeated 3, 6, 12 and 30 times, 280 μl of an aqueous glucose solution containing 20 mg/dl of glucose is fed and the oxidation current is determined.

From the data of oxidation current thus obtained, the values of relative detection sensitivity are calculated according to the following equation:

$$R.D.S.* = \frac{\text{oxidation current determined with glucose solution after feeding of serum samples}}{\text{oxidation current determined with glucose solution before feeding of serum samples}} \times 100$$

R.D.S. = relative detection sensitivity

The results are shown in Table 3 below.

TABLE 3

| Number of serum sample feedings | Relative detection sensitivity |
|---|---|
| 3 | 85.3 |
| 6 | 78.5 |
| 12 | 70.3 |
| 30 | 65.2 |

It can be seen from Table 3 that, if serum samples are analyzed one after another without removal of proteins and non-glucose reducing substances present in the samples, the relative detection sensitivity decreases outstandingly with the number of feedings of the liquid samples.

EXAMPLE 2

Figure 6:
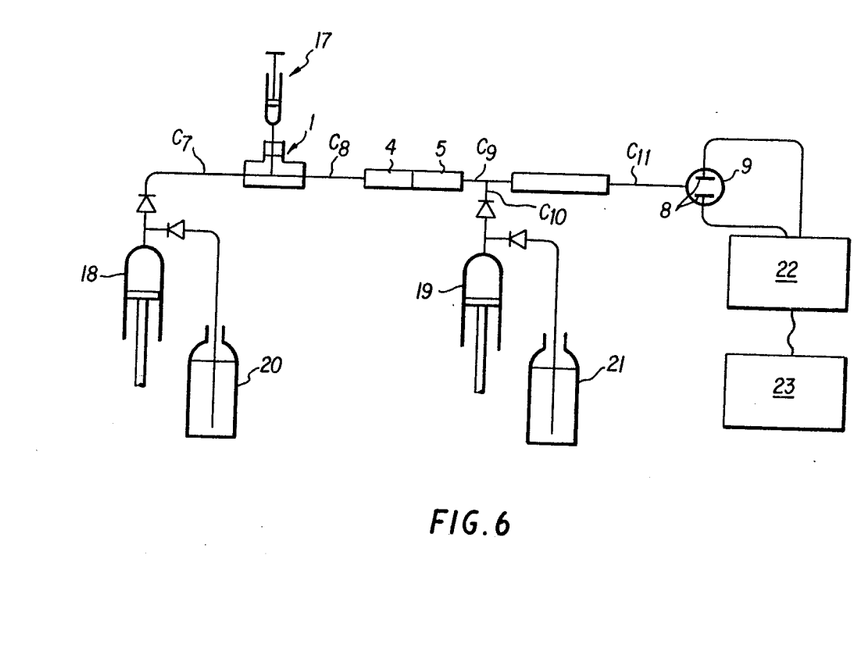

The glucose content of serum is analyzed with the apparatus shown in FIG. 6. An ion exchange column is 3 mm in inner diameter and 100 mm in length. The first half of the column (50 mm) is packed with Diaion PA 310 (Cl-form), while the latter half of the column (50 mm) is packed with Amberlite 200 C (Na-form). Thus, the column is used as anion exchange resin column 4 and cation exchange resin column 5.

As the glucose oxidase column 6, a glass column of 3 mm in diameter and 100 mm in length is used and packed with an immobilized glucose oxidase prepared in accordance with a procedure described below.

The analysis is effected as follows:

At first, using a microsyringe 17, 5 $\mu l$ of serum is introduced through the sample inlet 1 into conduit $c_8$. Then, a voltage of 0.5 volt is applied to the working electrode of the amperometric detector 9, and, at the same time, pump for water 18 and pump for a buffer solution 19 begin to work 20 and 21 designate the containers from which the water and buffer solution respectively are pumped into conduits $c_7$ and $c_{10}$. Conduit $c_7$ leads into the conduit $c_8$ at the sample inlet 1. Conduit $c_{10}$ joins conduit $c_9$ at a location between columns 5 and 6. The sample, flows from column 6 to amperometric detector 9 through conduit $c_{11}$. Suitable valves are also indicated in FIG. 6. The pumps for water and the buffer solution which are reciprocating pumps are worked for 15 seconds at a discharge rate of 5 ml/min. and 1 ml/min., respectively. The current flowing through the working electrode in the amperometric detector is detected as the maximum oxidation current through circuit for detecting the maximum oxidation current 22 and displayed on recorder 23. After 15 seconds, the polarity of the detection electrodes is automatically reversed, while the pumps for water and the buffer solution are worked for 5 seconds at a discharge rate of 20 ml/min. and 4 ml/min., respectively. In order to wash the system quickly, the discharge rates of the pumps are increased. Upon completion of the discharge stage, the pumps enter into the suction stage. After the suction of an amount of water or the buffer solution corresponding to that of the discharge, each pump stops working. The time required for completing the suction from the start of the discharge of the pump is about 29 seconds, during which time the pumps works automatically according to the prescribed time schedule. FIG. 7 illustrates changes with the passage of time in the voltage applied to the working electrode, the current flowing through the working electrode, and a state of the discharge and suction of the pumps in this example.

When the relationship between the concentration of glucose in a sample and the maximum oxidation current is determined using a standard serum shown in Table 4, it is found that there is a linear relationship between them, and that a current of 1 $\mu A$ corresponds to a glucose concentration of 69.0 mg/dl.

An average concentration of glucose is determined by analyzing it five times with a standard serum shown in Table 5. The results are shown in Table 5.

TABLE 4

| Standard serum | Glucose concentration*[1] (mg/dl) | Maximum oxidation current ($\mu A$) |
|---|---|---|
| Pathonorm-L*[2] | 27 | 0.041 |
| Seronorm*[3] | 125 | 0.17 |
| Q-PAK-II*[4] | 201 | 0.29 |
| Pathonorm-H*[5] | 256 | 0.39 |

TABLE 5

| Standard serum | Glucose Concentration (mg/dl) | Average maximum oxidation current ($\mu A$) | Range*[9] ($\mu A$) | Glucose concentration (Measured value) (mg/dl) |
|---|---|---|---|---|
| Q-PAK-I*[6] | 97 | 0.14 | 0.01 | 97 |
| Precilip*[7] | 105 | 0.15 | 0.01 | 104 |
| Stable-N*[8] | 125 | 0.18 | 0.01 | 124 |

*[1] a value analyzed by a manufacturer
*[2], *[3] and *[5] a trademark of Nyegaard & Co. As. Oslo (Normay)
*[4] and *[6] a trademark of Hyland (Div. Travenol Laboratories Inc.)
*[7] a trademark of Boehringer Mannheim
*[8] a trademark of Chugai Pharmaceutics Co., Ltd.
*[9] a difference between the maximum and minimum values in an analysis which is repeated five times.

The immobilized glucose oxidase used in this example is prepared as follows:

To 10 g of a 10 wt. % aqueous solution of polyvinyl pyrrolidone having an average molecular weight of 360,000 is added 0.8 g of pentaerythritol triacrylate with stirring. To this mixture is added a solution of 0.11 g of benzoin methyl ether, 0.055 g of sodium dodecyl sulfate and 2 g of methyl cellsolve with stirring to give an emulsion. This emulsion (0.2 g) is mixed with 0.2 ml of a solution of glucose oxidase (20 mg/ml) in 0.1 M phosphate buffer solution (pH 6.2) with stirring to give an emulsion containing the enzyme. The emulsion and 3.5 g of glass beads having an average diameter of 0.6 mm are mixed to moisten the beads uniformerly. The beads are spread to give a single layer of the beads, and then air-dried at room temperature for one hour. The beads are exposed in the air for 5 minutes to the light from a 2 KW ultra-high pressure mercury lamp (wave lengths: 300–500 nm, bright lines: 365 nm, 405 nm, 436 nm) which is 50 cm distant from the beads.

Having now fully described the invention, it will be apparent to one of ordinary skill in the art that many changes and modifications can be made thereto without departing from the spirit of the invention as set forth herein.

What is claimed as new and intended to be covered by letters patent is:

1. In a method of measuring glucose content, in which the glucose content of a liquid sample is analyzed by contacting the glucose-containing liquid sample with glucose oxidase to produce hydrogen peroxide and the amount of hydrogen peroxide produced is determined, the improvement comprising pretreating the liquid sample with the salt form of a strongly basic anion exchange resin and the salt form of a strongly acidic cation exchange resin, then contacting the sample with glucose oxidase to produce hydrogen peroxide in amount proportional to the glucose present in the sample and determining the amount of hydrogen peroxide produced through detection electrodes to which an alternating voltage of rectangular wave form is applied thereby generating an oxidation current proportional to the amount of hydrogen peroxide present in the sample located at the detection electrodes and detecting said oxidation current.

2. The method according to claim 1 wherein the voltage of rectangular wave form has a frequency in the range of 0.001 to 50 Hz and in which the sample contacts the salt form of the strongly basic anion exchange resin before it contacts the salt form of the strongly acidic cation exchange resin.

3. The method according to claim 1 wherein the liquid sample is treated first with the salt form of a strongly basic anion exchange resin and then with the salt form of a strongly acidic cation exchange resin.

4. The method according to claim 1 wherein the ion exchange resins are porous, highly porous or macroreticular ion exchange resins.

5. The method according to claim 1 wherein the strongly basic anion exchange resin is in the chloride form and the strongly acidic cation exchange resin in the sodium form.

6. The method of claim 1 wherein said liquid sample is a urine or blood serum containing sample.

7. The method according to claim 1, wherein the sample is admixed with a buffer solution after pretreatment with ion exchange resins followed by contact with glucose oxidase.

8. The method according to claim 1, wherein the voltage of rectangular wave form has a frequency in the range of 0.001 to 50 Hz and in which after the sample contacts the salt form of the strongly basic anion exchange resin and then the salt form of the strongly acidic cation exchange resin, the sample is admixed with a buffer solution and then contacts glucose oxidase.

9. An apparatus for measuring glucose content, which involves:
(a) an ion exchange resin column section of at least one column of the salt form of a strongly basic anion exchange resin and the salt form of a strongly acidic cation exchange resin, the columns of said column section being in series when there is more than one column in the section, and an inlet conduit and an outlet conduit joined to the column section for passing a glucose-containing liquid sample therethrough,
(b) means for supplying a buffer solution to said liquid sample while it is passing through said outlet conduit joined to the ion exchange resin column section, said means including a buffer solution conduit joined to the outlet conduit at a location between its termini,
(c) a column of immobilized glucose oxidase attached to the terminus of said outlet conduit distant from the ion exchange resin column section for passing therethrough the liquid sample, after it has left the column of said ion exchange resin and then has been diluted with a buffer solution, to produce hydrogen peroxide by contacting the liquid sample with glucose-oxidase,
(d) an amperometric detector with detection electrodes to which an alternating voltage of rectangular wave form is applied, for determining the amount of hydrogen peroxide contained in the liquid sample which has left the column of immobilized glucose oxidase and a conduit joining the glucose oxidase to the amperometric detector for delivering the liquid sample to the amperometric detector.

10. The apparatus of claim 9 which includes also conduit means for supplying air to the sample in the apparatus at the location in the outlet conduit of the ion exchange resin column section where the buffer conduit joins it, and which further includes a conduit exit means attached to the amperometric detector for permitting the sample to exit from the amperometric detector and pump means for forcing the sample, the buffer solution and the air to flow through the apparatus, and which includes air vent means between the exit of the column of immobilized glucose oxidase and the amperometric detector.

11. The apparatus of claim 9 wherein the amperometric detector includes a means for applying said alternating rectangular voltage waves at a frequency in the range of 0.001 to 50 Hz to the electrodes.

* * * * *